US006369030B1

United States Patent
Cole et al.

(10) Patent No.: US 6,369,030 B1
(45) Date of Patent: Apr. 9, 2002

(54) INHIBITORS OF HISTONE ACETYLTRANSFERASES (HATS) AND USES THEREOF

(75) Inventors: Philip A. Cole, Baltimore, MD (US); Raymond E. Soccio, New York, NY (US); Ontario D. Lau, Brooklyn, NY (US); Ehab M. Khalil, Bronx, NY (US); Tapas K. Kundu, Karnataka (IN); Robert G. Roeder, New York, NY (US)

(73) Assignee: The Rockfeller University, New York, NY (US)

( * ) Notice: Subject to any disclaimer, the term of this patent is extended or adjusted under 35 U.S.C. 154(b) by 0 days.

(21) Appl. No.: 09/451,034

(22) Filed: Nov. 29, 1999

(51) Int. Cl.$^7$ .............................. A61K 38/00; C07K 1/00
(52) U.S. Cl. .............................. 514/12; 514/15; 514/16; 514/17; 530/324; 530/326; 530/328; 530/329; 530/330; 530/345
(58) Field of Search .............................. 514/12, 15, 16, 514/17; 530/324, 326, 328, 329, 330, 345

(56) References Cited

PUBLICATIONS

Smith et al., *Proc. Natl. Acad. Sci. USA.*, vol. 95, pp. 3561–3565, Mar. 1998.*
Kuo et al., *Nature*, vol. 383, pp. 269–277, Sep. 19, 1996.*
Tanner et al., *The Journal of Biological Chemistry*, vol. 274, No. 26, pp. 18157–18160, Jun. 25, 1999.*
Thorne et al., *Eur. J. Biochemi.*, vol. 193, pp. 701–713, 1990.*
Sobel et al., *Proc. Natl. Acad. Sci. USA.*, vol. 92 pp. 1237–1241, Feb. 1995.*

Cullis, P. M., et al. (1982) Inhibition of histone acetylation by N–[2–S–(S–Coenzyme A)acetyl] spermidine amide, a multisubstrate analog. J. Biol. Chem. 257, 12165–12169.
DeAngelis, J. et al. (1998) Kinetic analysis of the catalytic mechanism of serotonin N–acetyltransferase. J. Biol. Chem. 273, 3045–3050.
Erwin, B. G., et al. (1984) Differential inhibition of histone and polyamine acetylases by multisubstrate analogs. Biochemistry 23, 4250–4255.
Khalil, E., and Cole, P. A. (1998) A potent inhibitor of the melatonin rhythm enzyme. J. Am. Chem. Soc. 120, 6195–6196.
Khalil, E., et al. (1999) Mechanism–based inhibition of the melatonin rhythm enzyme: pharmacologic exploitation of active site functional plasticity. Proc. Natl. Acad. Sci. USA, 96, 12418–12423.
Schiltz, R. L., et al. (1999) Overlapping but distinct patterns of histone acetylation by the human coactivators p300 and PCAF within nucleosomal substrates. J. Biol. Chem. 274, 1189–1192.
Tanner, K. G., et al. (1999) Catalytic mechanism and function of invariant glutamic acid 173 from the histone acetyltransferase GCN5 transcriptional coactivator. J. Biol. Chem. 274, 18157–18160.
Taunton, J., et al. (1996) A mammalian histone deacetylase related to the yeast transcriptional regulator. Science 272, 408–411.

* cited by examiner

*Primary Examiner*—Christopher S. F. Low
*Assistant Examiner*—Abdel A. Mohamed
(74) *Attorney, Agent, or Firm*—Klauber & Jackson (57) ABSTRACT

Histone acetyltransferase inhibitors, especially those that are differentiate between p300 and PCAF histone acetyltransferase; also therapeutic processes comprising their administration to humans.

2 Claims, 9 Drawing Sheets n=0-8

$R_1 - R_7$ = methyl, ethyl, propyl, butyl, pentyl, vinyl, ethinyl, allyl, methyloxy, ethyloxy, propyloxy butyloxy, pentyloxy Also, $R_3$ and $R_4$ = fluoro, chloro, bromo, iodo, carboxy, hydroxy, oxo

FIG. 5 acetyl-CoA

FIG. 6

Lys-CoA

FIG. 7

$R_1$–$R_7$ = methyl, ethyl, propyl, butyl, pentyl, vinyl, ethinyl, allyl, methyloxy, ethyloxy, propyloxy, butyloxy, pentyloxy Also, $R_3$ and $R_4$ = fluoro, chloro, bromo, iodo, carboxy, hydroxy, oxo

SEQUENCE LISTING

<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: PART OF
       SYNTHETIC MOLECULES THAT ACT AS ENZYME INHIBITORS

<400> SEQUENCE: 1

Thr Ala Arg Lys Ser Thr Gly Gly
 1               5

-continued

```
<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: PART OF
      SYNTHETIC MOLECULES THAT ACT AS ENZYME INHIBITORS

<400> SEQUENCE: 2

Ala Pro Arg Lys Gln
  1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: PART OF
      SYNTHETIC MOLECULES THAT ACT AS ENZYME INHIBITORS
<223> OTHER INFORMATION: The first Ala is a modified residue; it is
      acetylated

<400> SEQUENCE: 3

Ala Arg Thr Thr Lys Gln Thr Ala Arg Lys Ser Thr Gly
  1               5                  10

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: PART OF
      SYNTHETIC MOLECULES THAT ACT AS ENZYME INHIBITORS

<400> SEQUENCE: 4

Ala Pro Arg Lys Gln Leu
  1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: PART OF
      SYNTHETIC MOLECULES THAT ACT AS ENZYME INHIBITORS

<400> SEQUENCE: 5

Ala Pro Arg Lys
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: PART OF
      SYNTHETIC MOLECULES THAT ACT AS ENZYME INHIBITORS

<400> SEQUENCE: 6

Gly Leu Gly Lys
  1

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: PART OF
```

```
        SYNTHETIC MOLECULES THAT ACT AS ENZYME INHIBITORS
<223>   OTHER INFORMATION: The first ala is a modified residue; it is
        acetylated

<400>   SEQUENCE: 7

Ala Arg Thr Lys Gln Thr Ala Arg Lys Ser Thr Gly
 1               5                  10

<210>   SEQ ID NO 8
<211>   LENGTH: 13
<212>   TYPE: PRT
<213>   ORGANISM: Artificial Sequence
<220>   FEATURE:
<223>   OTHER INFORMATION: Description of Artificial Sequence: PART OF
        SYNTHETIC MOLECULES THAT ACT AS ENZYME INHIBITORS
<223>   OTHER INFORMATION: The first ala is a modified residue; it is
        acetylated.

<400>   SEQUENCE: 8

Ala Arg Thr Lys Gln Thr Ala Arg Lys Ser Thr Gly Gly
 1               5                  10

<210>   SEQ ID NO 9
<211>   LENGTH: 7
<212>   TYPE: PRT
<213>   ORGANISM: Artificial Sequence
<220>   FEATURE:
<223>   OTHER INFORMATION: Description of Artificial Sequence: PART OF
        SYNTHETIC MOLECULES THAT ACT AS ENZYME INHIBITORS
<223>   OTHER INFORMATION: SER is a modified residue and is acetylated

<400>   SEQUENCE: 9

Ser Gly Arg Gly Lys Gly Gly
 1               5

<210>   SEQ ID NO 10
<211>   LENGTH: 12
<212>   TYPE: PRT
<213>   ORGANISM: Artificial Sequence
<220>   FEATURE:
<223>   OTHER INFORMATION: Description of Artificial Sequence: PART OF
        SYNTHETIC MOLECULES THAT ACT AS ENZYME INHIBITORS

<400>   SEQUENCE: 10

Gly Leu Gly Lys Gly Gly Ala Lys Arg Asn Arg Ala
 1               5                  10

<210>   SEQ ID NO 11
<211>   LENGTH: 7
<212>   TYPE: PRT
<213>   ORGANISM: Artificial Sequence
<220>   FEATURE:
<223>   OTHER INFORMATION: Description of Artificial Sequence: SYNTHETIC
        MOLECULE THAT ACT AS ENZYME INHIBITOR
<223>   OTHER INFORMATION: G in position 1 is a modified residue and is
        acetylated.  The K in position 3 is a modified
        residue and is conjugated via its epsilon NH2
        group to coenzyme A.

<400>   SEQUENCE: 11

Gly Gly Lys Ala Pro Arg Lys
 1               5

<210>   SEQ ID NO 12
<211>   LENGTH: 7
<212>   TYPE: PRT
<213>   ORGANISM: Artificial Sequence
<220>   FEATURE:
<223>   OTHER INFORMATION: Description of Artificial Sequence: SYNTHETIC
```

```
      MOLECULE THAT ACT AS ENZYME INHIBITOR
<223> OTHER INFORMATION: G in position 1 is a modified residue and is
      aceylated.  The K in position 3 is a modified
      residue and is conjugated via its epsilon NH2
      group to coenzyme A

<400> SEQUENCE: 12

Gly Gly Lys Gly Leu Gly Lys
  1               5

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      MOLECULE THAT ACT AS ENZYME INHIBITOR
<223> OTHER INFORMATION: The A in position 1 is a modified residue and
      is aceylated. The K in position 4 is a modified
      residue and is conjugated via its epsilon NH2
      group to coenzyme A.

<400> SEQUENCE: 13

Ala Arg Thr Lys Gln Thr Ala Arg Lys Ser Thr Gly Gly Lys Ala Pro
  1               5                  10                  15

Arg Lys Gln Leu
            20

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: SYNTHETIC
      MOLECULE THAT ACT AS ENZYME INHIBITOR
<223> OTHER INFORMATION: The S in position 1 is a modified residue and
      is acetylated.  The K in position 8 is a modified
      residue and is conjugated via ita epsilon NH2
      group to coenzyme A.

<400> SEQUENCE: 14

Ser Gly Arg Gly Lys Gly Gly Lys Gly Leu Gly Lys Gly Gly Ala Lys
  1               5                  10                  15

Arg Asn Arg Ala
            20
```

INHIBITORS OF HISTONE ACETYLTRANSFERASES (HATS) AND USES THEREOF

The research leading to the present invention was supported, at least in part, by grant CA42567 from the National Cancer Institute, also by funds from the NIH Medical Scientist Training Program (grant number GM07739). Accordingly, the Government may have certain rights in the invention.

BACKGROUND

This invention relates to the field of enzyme inhibitors, especially inhibitors of histone acetyltransferases.

The molecular identification of a number of histone acetyltransferases (HATs) has led to new insights into the mechanisms of activation of gene expression (Mizzen and Allis, 1998; Stuhl, 1998). The members of this growing family include the important transcription factors p300/CBP and PCAF (Yang et al., 1996; Ogryzko et al., 1996; Bannister and Kouzarides, 1996). PCAF and p300/CBP can catalyze the acetylation of histones (Yang et al., 1996; Ogryzko et al., 1996; Bannister and Kouzarides, 1996) and other substrates (Wu and Roeder, 1997) and these HATs have been suggested to play differential roles in coactivation of gene expression. The HAT domain of PCAF appears to be involved in MyoD-dependent coactivation and differentiation, whereas that of p300 seems to be less important (Puri et al., 1997). A role for the acetyltransferase activity of PCAF was also suggested for transcriptional activation by the liganded retinoic acid receptor (RAR). The PCAF acetyltransferase domain but not that of CBP can assist retinoic acid induced transcription in cultured cells that are depleted of endogenous PCAF and CBP by antibody microinjection (Korzus et al., 1998). On the other hand, the acetyltransferase domain of CBP and not that of PCAF can contribute to CREB-activated transcription in PCAF- and CBP-depleted cells (Korzus et al., 1998). These experiments suggest differential requirements for PCAF and p300/CBP in the coactivation of various sequence-specific DNA binding transcriptional activators. However, none of these studies has established directly that acetyltransferase action or histone acetylation per se is involved in these activation processes.

Because of the possibility that PCAF and p300 proteins physically interact (Ogryzko et al., 1996), their relative contributions toward acetylation of substrates and gene activation is not generally known. While mutations in the active site regions of these enzymes can help clarify these issues, the effects of such mutations on altering protein structure and stability can complicate interpretations. Small molecules have been useful in elucidation of the general role of histone acetylation in transcription by blocking histone deacetylase (Taunton et al., 1996). It would be advantageous to apply active-site directed, specific, and potent synthetic inhibitors of individual HAT enzymes to dissect their relative roles in protein acetylation and transcription. Furthermore, there is a basis for expecting that the blockade of p300 HAT activity would have therapeutic potential in the treatment of certain cancers (Giles et al., 1998).

Prior to the molecular characterization of specific HAT enzymes, several polyamine-CoA conjugates were found to block HAT activities present in cell extracts (Cullis et al., 1982; Erwin et al., 1984). However the actual enzyme or enzymes inhibited have not been characterized. We have shown that one of these synthetic inhibitors (Cullis et al., 1982) potently blocks non-chromatin template mediated transcription and therefore would not be useful in the determination of the role of HAT activity in gene activation unpublished data.

PCAF belongs to a superfamily of GNAT (GCN-5 related N-acetyltransferases) acetyltransferases whose three-dimensional structures have recently been reported (Coon et al., 1995; Neuwald and Landsman, 1997; Wolf et al., 1998; Dutnall et al., 1998; Wybenga-Groot et al., 1999; Hickman et al., 1999a; Hickman et al., 1999b; Lin et al., 1999). Family members most likely catalyze acetyl transfer in a ternary complex containing enzyme, histone, and acetyl-CoA (De Angelis et al., 1998; Tanner et al., 1999). Bisubstrate analog inhibitors have proved successful for the GNAT family member serotonin N-acetyltransferase (Khalil et al., 1998; Khalil et al., 1999). Here we report on bisubstrate analog inhibitors and their effects on histone acetylation and transcription.

SUMMARY OF THE INVENTION

The invention in a general aspect is a histone acetyltransferase inhibitor. Such inhibitors are useful both as analytical reagents for studying the role of histone acetyltransferases in the regulation of gene expression. They are also useful for inhibiting acetyltransferase in diseased cells that overexpress such acetyltransferase.

In a particular embodiment of the invention, the inhibitor is Coenzyme A (CoA) covalently linked (preferably via a —CO— bridge to a lysine $\epsilon$-amino group) to lysine or a polypeptide comprising lysine. Inhibitors that are specific for p300 acetyltransferase are those in which the CoA is linked to lysine or a very short polypeptide (2 to 6 amino acids) comprising lysine. Such inhibitors will inhibit p300 acetyltransferases ("p300 inhibitors") more significantly (at least 100 times as much) than they inhibit PCAF acetyltransferases. Inhibitors that are specific for PCAF acetyltransferases ("PCAF inhibitors") are those in which the CoA is linked to lysine in longer polypeptides (8 or more amino acids.) Such inhibitors will inhibit PCAF acetyltransferases ("PCAF inhibitors") more significantly (at least 100 times as much) than they inhibit p300 acetyltransferases.

In another aspect, the invention is histone acetylase inhibitors that will inhibit transcription of a histone-associated DNA sequence more strongly than the identical DNA sequence not associated with histones (especially, naked DNA). Such inhibitors are the p300 inhibitors and PCAF inhibitors.

In another general aspect, the invention is the process of administering a histone acetyltransferase inhibitor to a host, the host being an animal or human. Such a process is done for therapeutic purposes in cases where it is beneficial to the host to have a histone acetyltransferase inhibited. That is the case, for example, in certain types of cancers. It can also be the case in certain gene therapy protocols.

A preferred histone acetyltransferase inhibitor of the present invention is one with the structure where the H is [CHR$_{11}$] is absent if R$_{11}$ is oxygen
where n is an integer in the range 0 to 2;
where R$_1$, R$_2$, and R$_{10}$ are independently selected from the group consisting of hydrogen, methyl, ethyl, propyl, butyl, pentyl, vinyl, ethinyl, allyl, methyloxy, ethyloxy, propyloxy, butyloxy, and pentyloxy;
where R$_{11}$ for each R$_{11}$ is independently selected (e.g., if n is 3, there are three R$_{11}$ moieties that can be independently selected) from the group consisting of hydrogen, methyl, ethyl, propyl, butyl, pentyl, vinyl, ethinyl, allyl, methyloxy, ethyloxy, propyloxy, butyloxy, pentyloxy fluoro, chloro, bromo, iodo, hydroxy, carboxy, and oxygen,
where carboxy is wherein R$_{12}$ is hydrogen, methyl, ethyl, propyl, or isopropyl,
where R$_8$ is selected from the group consisting of methyl, ethyl, propyl, butyl, pentyl, vinyl, ethinyl, allyl, methyloxy, ethyloxy, propyloxy, butyloxy, pentyloxy, an amino acid or a polypeptide comprising two amino acids, provided that if R$_8$ is an amino acid or polypeptide, said amino acid or polypeptide may have a protective group (e.g., it is acetylated) at its N terminus. The intent of the protective group is to provide ptrotection during the compound's synthesis.
Where R$_9$ is selected from the group consisting of methyl, ethyl, propyl, butyl, pentyl, vinyl, ethinyl, allyl, methyloxy, ethyloxy, propyloxy, butyloxy, pentyloxy, an amino acid acetylated at its N terminus, or a polypeptide of two or more amino acids; and pharmaceutically acceptable salts thereof.

Figure 7:
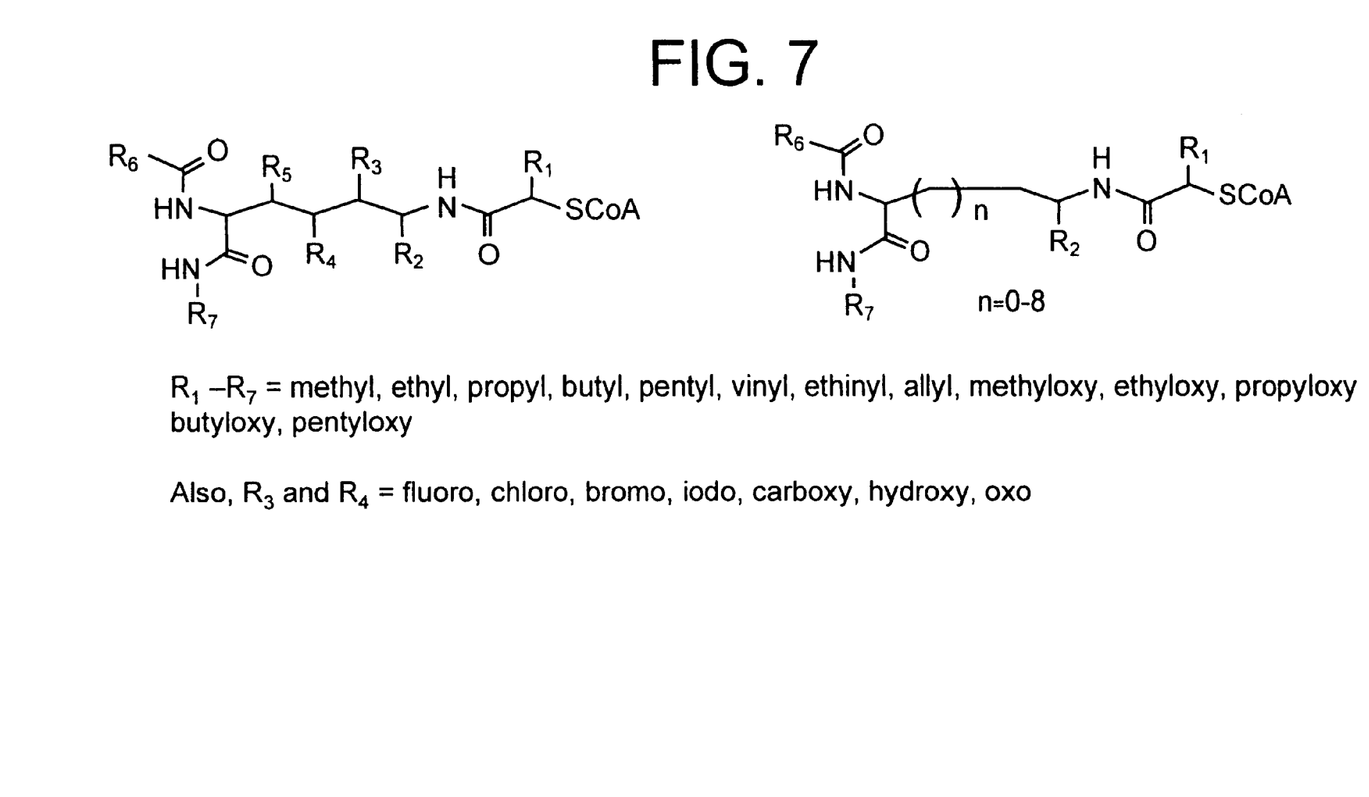
FIG. 7. Inhibitory lysine analogs.

Inhibitors of interest that are analogs of Lys-CoA are also shown in FIG. 7, (R$_6$ and R$_7$ in FIG. 7 correspond to R$_8$ and R$_9$, respectively.) For H3-20-CoA analogs of interest include those with substitutions in the lysine moiety similar to those shown for Lys-CoA. In addition, truncations and substitutions of the other amino acids in the peptide backbone using combinatorial approaches can be performed to create analogs.

Specific embodiments of interest are:
those wherein R$_8$, in combination with the carbonyl group adjacent to R$_8$, is an amino acid or a polypeptide of two or more amino acids;
those wherein R$_9$ is an amino acid or a polypeptide of two or more amino acids;
those wherein R$_8$, in combination with the carbonyl group adjacent to R$_8$, is an amino acid of a polypeptide of two or more amino acids, and R$_9$ is an amino acid or a polypeptide of two or more amino acids.

Specific inhibitors of p300 acetyltransferase are preferably:

those wherein R$_8$, in combination with the carbonyl group adjacent to R$_8$, is an amino acid, especially where the amino acid is Gly;
those wherein R$_9$ is an amino acid or a polypeptide of 2 or 3 amino acids, especially where R$_9$ is selected from the group consisting of Gly, Gly-Leu, and Gly-Lys-Gly (such that the leftmost amino acid is the one closest to the NH group adjacent to the R$_9$ group); and
those where wherein R$_8$ is methyl and R$_9$ is hydrogen (also referred to as Lys-CoA herein).

Specific inhibitors of PCAF acetyltransferase are preferably:
those wherein R$_8$, in combination with the carbonyl group adjacent to R$_8$, is a polypeptide comprising at least three amino acids, especially where the three amino acids are those of Gly-Gly-Thr and in that sequence;
those wherein R$_8$, in combination with the carbonyl group adjacent to R$_8$, comprises a polypeptide of at least 8 amino acids especially where the eight amino acids are those of Thr-Ala-Arg-Lys-Ser-Thr-Gly-Gly- (SEQ ID NO:1) and in that sequence:
those wherein R9 is a polypeptide of at least 5 amino acids, especially where the 5 amino acids are those of Ala-Pro-Arg-Lys-Gln (SEQ ID NO:2) and in that sequence; and
those where R8 is (N-acetyl)-Ala-Arg-Thr-Thr-Lys-Gln-Thr-Ala-Arg-Lys-Ser-Thr-Gly-NH-CH$_2$- in that sequence, wherein the peptide portion of R$_8$ is SEQ ID NO:3, and R9 is the polypeptide Ala-Pro-Arg-Lys-Gln-Leu (SEQ ID NO:4) in that sequence.

BRIEF DESCRIPTION OF THE DRAWINGS

FIG. 1. Design and synthesis of peptide CoA conjugates.

The sequence Ala-Pro-Arg-Lys is SEQ ID NO:5. The sequence Gly-Leu-gly-Lys is SEQ ID NO:6. The sequence Ala-Arg-Thr-Lys-Gln-Thr-Ala-Arg-Lys-Ser-Thr-Gly-Gly, which is represented in the Figure in reverse direction (from right to left), is SEQ ID NO:8. The sequence Ala-Pro-Arg-Lys-Gln-Leu is SEQ ID NO:4. The sequence Ser-Gly-Arg-Gly-Lys-Gly-Gly, which is represented in the Figure in reverse direction is SEQ ID NO:9. The sequence Gly-Leu-Gly-Lys-Gly-Gly-Ala-Lys-Arg-Asn-Arg-Ala is SEQ ID NO:10. The entire sequence for H3-CoA-7 is SEQ ID NO:11. The entire sequence for H4-CoA-7 is SEQ ID NO:12. The entire sequence for H3-CoA-20 is SEQ ID NO:13. The entire sequence for H4-CoA-20 is SEQ ID NO:14.

FIG. 3. Assessment of p300 and PCAF HAT activities in p300/PCAF.

FIG. 4. Lys-CoA inhibits p300 HAT activity dependent transcription activation.

FIG. 8. Evaluation of H3-CoA-20 as a HAT inhibitor.

DETAILED DESCRIPTION OF THE INVENTION

Amino acid abbreviations

"Ala" represents alanine, "Asn" represents asparagine, "Lys" represents lysine, "Leu" represents leucine. "Thr" represents threonine, "Ser" represents serine, "Arg" represents arginine, "Pro" represents proline, "Gln" represents glutamine.

Pharmaceutical aspects of the invention

Figure 6:
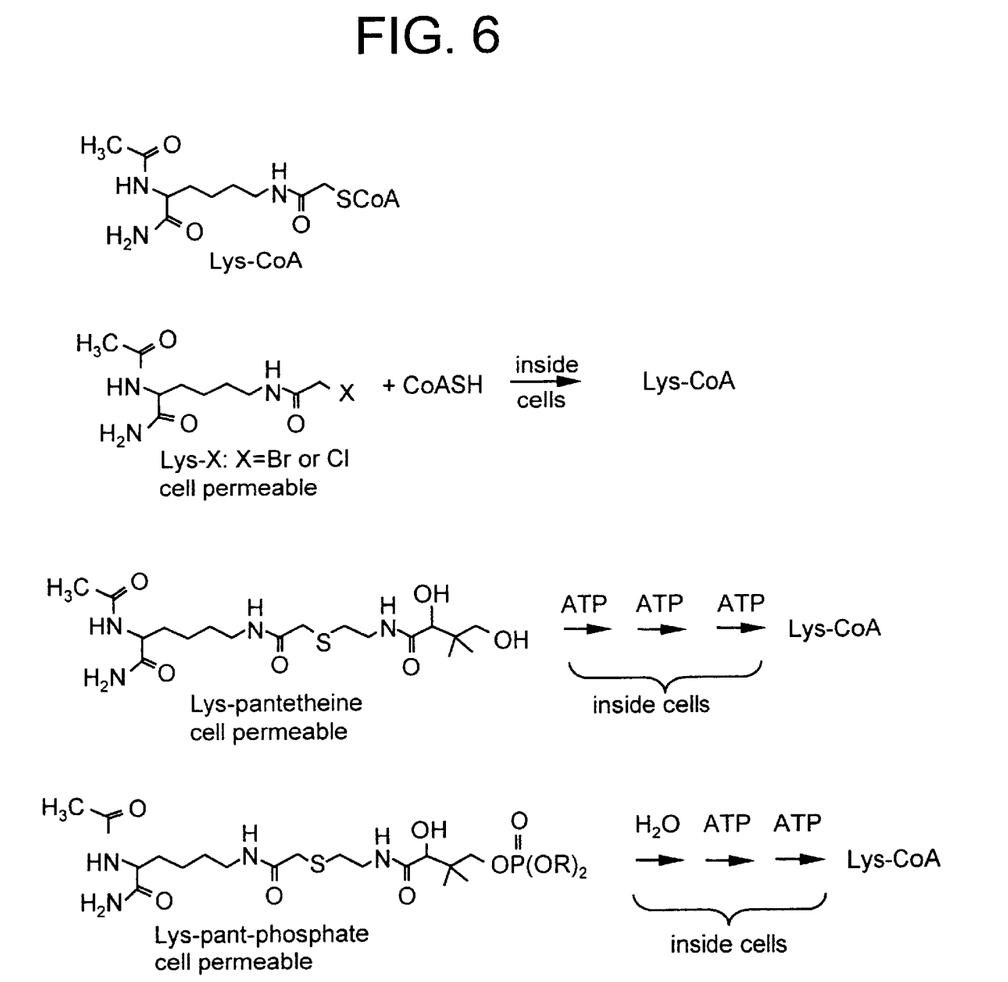
FIG. 6. Cell permeable analog development.

In a preferred embodiment, a prodrug represented by Lys-X is used in order that enzymes within the cell, especially HAT enzymes, can catalyze alkyl transfer to CoASH so as to generate the potent p300 inhibitor Lys-CoA within the cells. Lys-X is expected to be cell permeable because it is small, relatively hydrophobic and unchanged. Upon conversion to Lys-CoA within cells, it would be "trapped" in the cell and thereby a potent p300 inhibitor. (See FIG. 6.) This strategy was shown to be effective in a related system with serotonin N-acetyltransferase (E. M. Khalil et al., PNAS, vol. 96, pp. 12418–12423, 1999).

In another option, Lys-pantetheinyl derivatives are administered. The further elaboration of Lys-panteheine or Lys-pant-phosphate within cells can be predicted based on the known cellular enzymes that convert pantetheine and phosphopantetheine to coenzyme A. (See FIG. 6.) Indeed, we have shown (unpublished data) that this appears to take place for an indole-pantetheine derivative.

A general approach to making peptide agents cell permeable is to covalently attach them to short membrane permeable sequences (Rojas M. Donahue JP. Tan Z. Lin YZ. Genetic engineering of proteins with cell membrane permeability. Nature Biotechnology, 16(4):370–5, 1998 April and references therein). This is another option for both Lys-CoA and H3-20-CoA.

4) Liposomes and cationic lipids might also be used to deliver the HAT inhibitors inside cells.

Pharmaceutical preparations of the compounds of the invention would include pharmaceutically acceptable carriers, or other adjuvants as needed, and would be prepared in effective dosage ranges as needed.

Generally, the inhibitors (or precursors thereof capable of being correctly processed in the host or the host's cells) of the invention may be formulated for intraarterial, intraperitoneal, intramuscular, subcutaneous, intravenous, oral, nasal, rectal, bucal, sublingual, pulmonary, topical, transdermal, or other routes of administration. Comprehended by the invention are pharmaceutical compositions comprising effective amounts of inhibitors of the invention together with pharmaceutically acceptable diluents, preservatives, solubilizers, emulsifiers, adjuvants and/or carriers. Such compositions include, for example, aqueous diluents of various buffer content, incorporation of the material into particulate preparations of polymeric compounds such as polylactic acid, polyglycolic acid, etc. or into liposomes. The compositions may be prepared in liquid form, or may be in dried powder, such as lyophilized form.

Solid dosage forms include tablets, capsules, pills, troches or lozenges, cachets or pellets. Also, liposomal or proteinoid encapsulation may be used to formulate the present compositions (as, for example, proteinoid microspheres). Liposomal encapsulation may be used and the liposomes may be derivatized with various polymers.

Appropriate dosage levels for treatment of various conditions in various patients will depend on the patient and the therapeutic purpose. Generally, for injection or infusion, dosage will be between 0.01 $\mu$g of biologically active inhibitor/kg body weight and 10 mg/kg. The dosing schedule may vary, depending on the circulation half-life of the inhibitor (or its precursor) whether, for example, the inhibitor is delivered by bolus dose or continuous infusion, and the formulation used.

Results and discussion

Figure 1A:
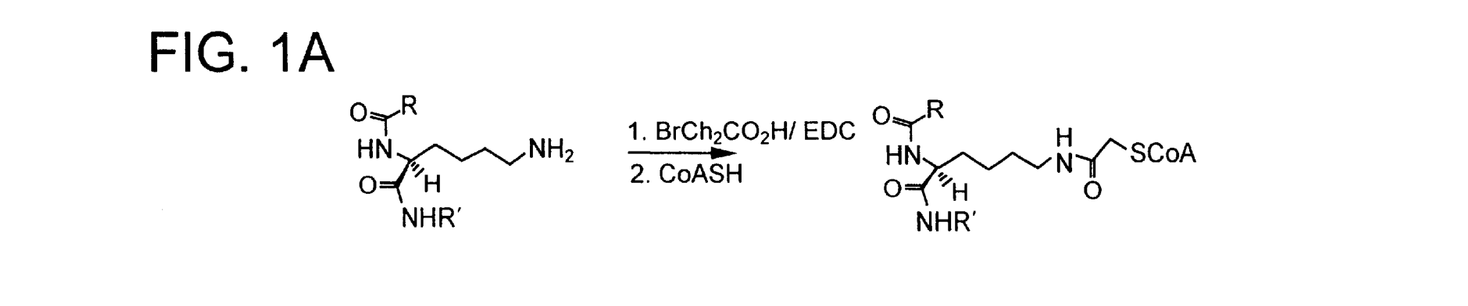
FIG. 1A: Coupling reactions.
Figure 1B:
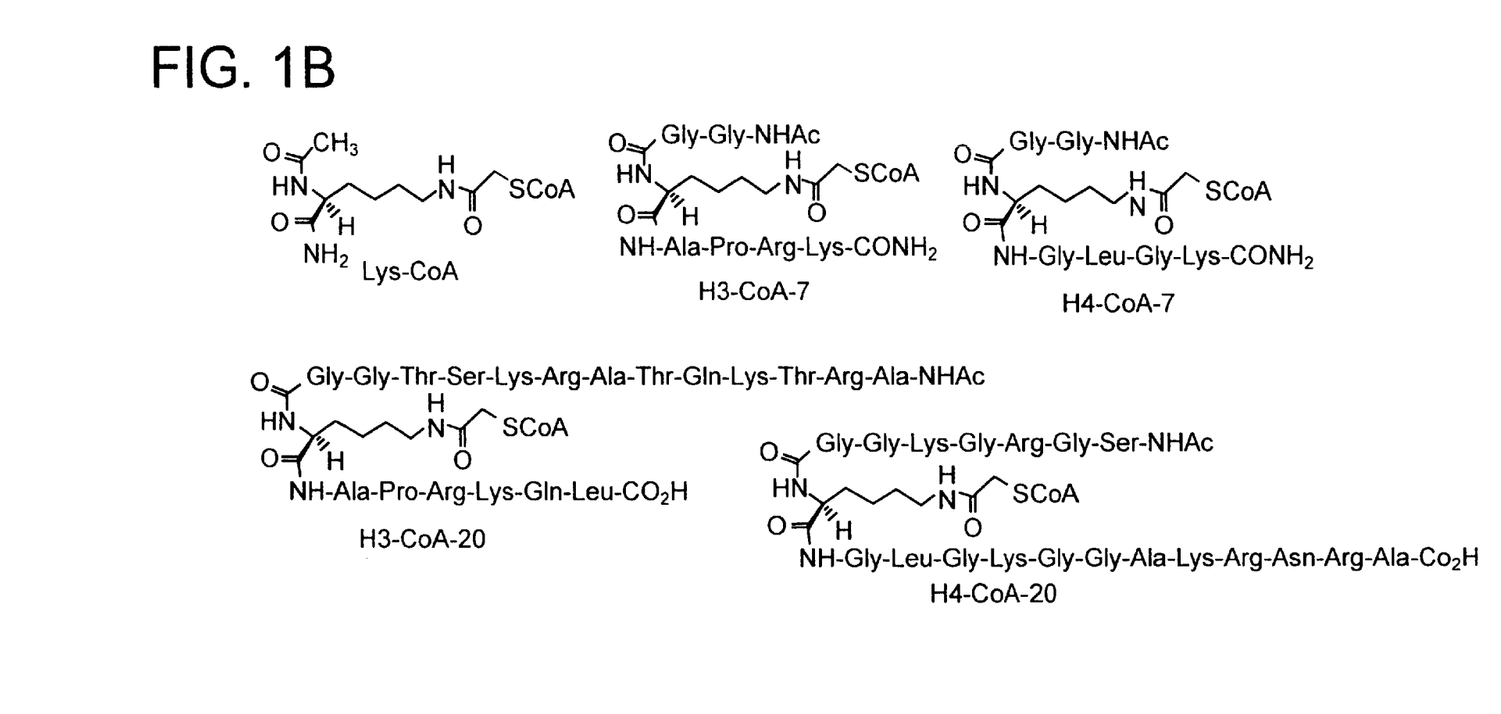
FIG. 1B: Peptide synthesis
FIG. 2. Evaluation of Lys-CoA as a HAT inhibitor.

We synthesized Lys-CoA and the other peptide CoA conjugates shown in FIG. 1. Modification of the $\epsilon$-amino group of the lysine was carried out in one pot, first coupling the amine with bromoacetic acid followed by reaction of the $\alpha$-bromo-acetamide function with CoASH (FIG. 1A). Partially, protected peptides were produced by solid phase peptide synthesis using the Fmoc strategy. Selective modification of the desired lysine in the context of other lysine residues was achieved using orthogonal protection with the dimethyldioxocyclohexylidene (Dde) protective group. It was necessary to carry out the CoA conjugation step after cleaving the peptides from the resin because of the presumed lability of the lycosidic linkage in CoA in the presence of strong acid conditions. Each peptide CoA conjugate (FIG. 1B) was purified to homogeneity (>95%) by reverse phase HPLC, and electrospray mass spectrometry was used to verify structural integrity. These compounds were stable in solution under long term storage conditions (>6 mos) at −80° C.

Figure 8A:
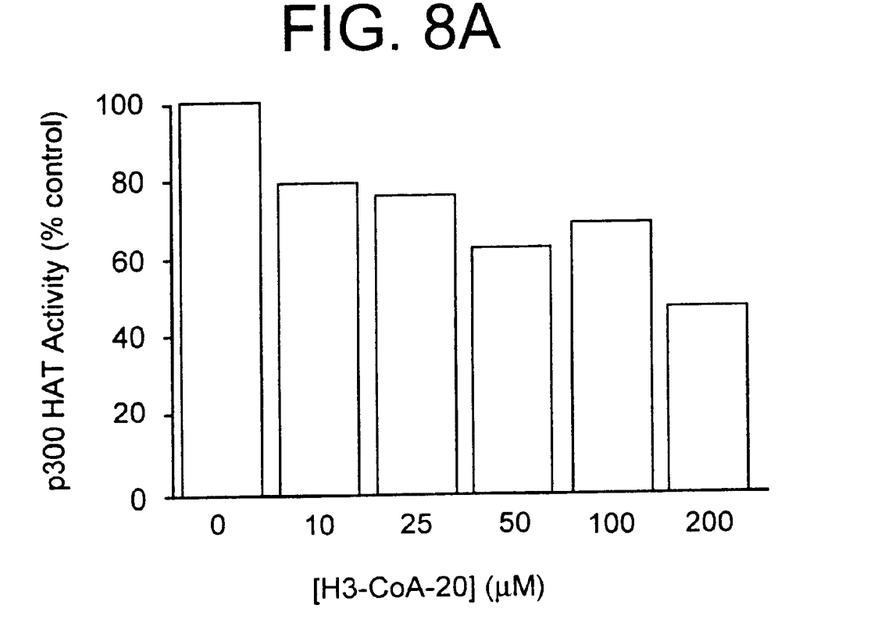
FIG. 8A: H3-CoA-20 p300 HAT inhibition.
Figure 8B:
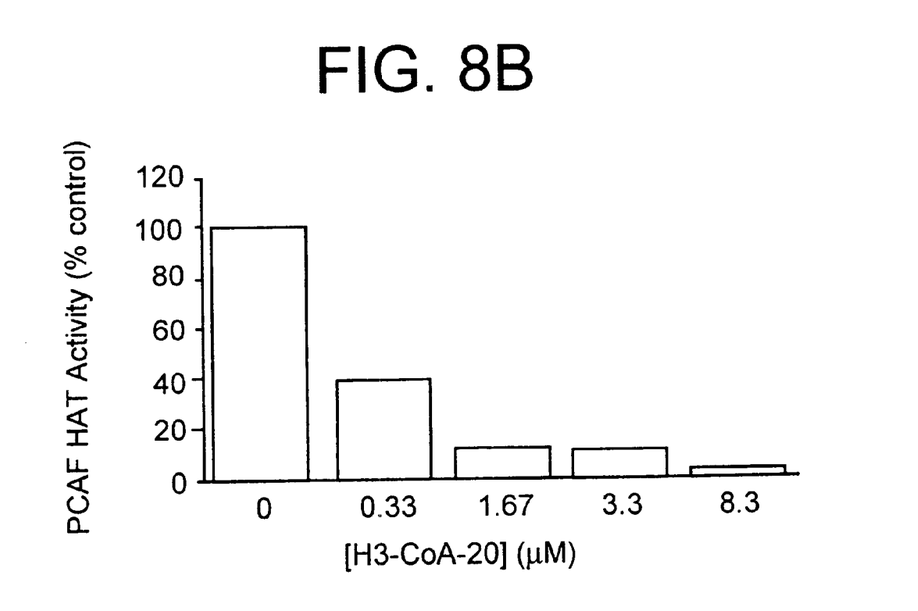
FIG. 8B: H3-CoA-20 PCAF inhibition.

Screening of the peptide CoA conjugate for inhibition of HAT activity of PCAF and p300 was carried out according to standard HAT assay procedures (Ogryzko et al., 1996; Yang et al., 1996; Schiltz et al., 1999) using commercially available mixed calf histone substrates. As can be seen, Lys-CoA was found to be a potent and selective inhibitor of p300 acetyltransferase activity with an $IC_{50}$ of approximately 500 nM (FIG. 2, Table 1). Under similar conditions, the $IC_{50}$ of Lys-CoA for PCAF inhibition was approximately 200 µM. Neither of the heptapeptide-CoA conjugates was effective at inhibiting p300 or PCAF (Table 1). H3-CoA-20 proved to be very effective at inhibiting PCAF HAT activity ($IC_{50}$=300 nM) but showed little ability to block p300 ($IC_{50}$=200 µM) (FIG. 8, Table 1). Interestingly, H4-CoA-20 was a poor inhibitor of both p300 and PCAF (Table 1). Neither the H3-20 peptide (which lacked CoA attachment) nor CoASH itself were potent HAT inhibitors (Table 1). That the H3-CoA-20 conjugate required the covalent attachment of the histone H3 20 amino acid peptide to CoASH was confirmed by showing that an equimolar mixture of free peptide and CoASH was poorly able ($IC_{50}$>10 µM) to block PCAF HAT activity (data not shown).

Regarding inhibition results with PCAF, there is enhanced inhibition by an H3-20-CoA conjugate over an H4-20-CoA conjugate, a degree of selectivity >100-fold). Inhibition of PCAF was not achieved by the shorter conjugate H3-CoA-7. This suggests that key binding interactions between the PCAF enzyme and the histone H3 substrate lie outside the nearest neighboring residues and are mediated more broadly over the substrate sequence.

The potent inhibition of p300 by Lys-CoA but by none of the other peptide-CoA conjugates was an unexpected finding. That incorporation of longer peptide sequences derived from the histone H4 or H3 substrate into the bisubstrate analog actually reduces binding affinity is not readily explicable. These results are particularly striking since Lys-CoA actually lacks positive charges, a hallmark of the N-terminal regions of the substrates histone H3 and histone H4. These findings strongly suggest that p300 has a significantly different catalytic mechanism or mode of substrate binding compared to PCAF and other GNAT superfamily members, reflecting its lack of sequence homology.

Figure 3A:
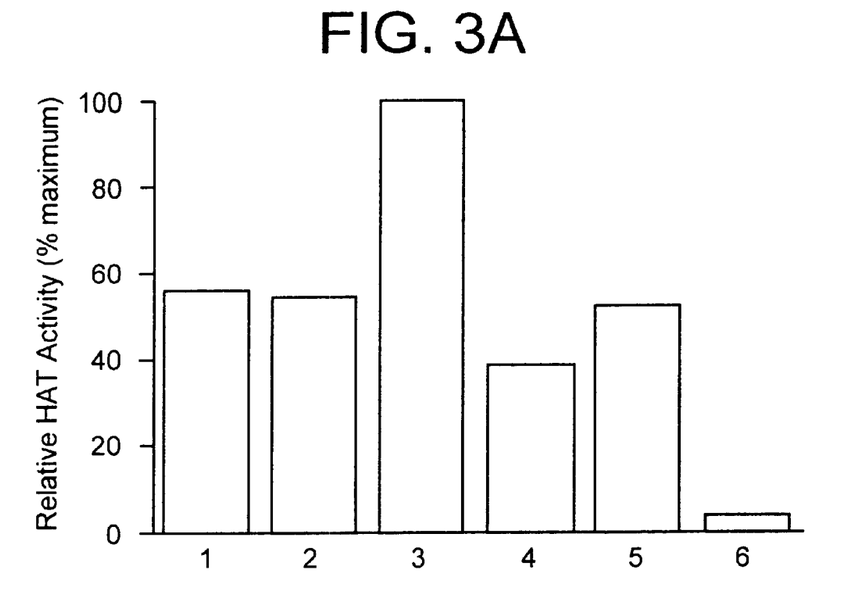
FIG. 3A: p300 and PCAF HAT activities with mixed histones as substrates. Bar 1, PCAF alone without inhibitors; Bar 2, p300 alone without inhibitors; Bar 3; PCAF+p300 without inhibitors; Bar 4, PCAF+p300+Lys-CoA (30 $\mu$M); Bar 5, PCAF+p300+H3-CoA-20 (30 $\mu$M); Bar 6, PCAF+p300+Lys-CoA (30 $\mu$M)+H3-CoA-20 (30 $\mu$M). Activities were normalized to 100% for Bar 3. Standard error was found to be ±20% for duplicate runs.

With potent and specific HAT inhibitors in hand, one can exploit these molecules in further biochemical analysis. Since p300 and PCAF may form a complex and since each catalyzes acetyltransferase activity, the availability of inhibitors allows an opportunity to investigate the precise contributions of each enzyme present in a PCAF/p300 mixture toward histone acetylation. As can be seen in FIG. 3A, the combination of PCAF and p300 (present together) leads to an increased histone acetylation rate compared to either enzyme working alone (compare bars 1 and 2 with bar 3). In principle, this increase could have arisen in two ways: i) simple summing of the two enzyme activities without synergism or antagonism, or ii) stimulation of enzyme A by enzyme B with concomitant antagonism of enzyme B by enzyme A. Here, application of Lys-CoA and H3-CoA-20 inhibitors proved useful in distinguishing between these possibilities. It was observed that in the presence of Lys-CoA, the PCAF/p300 mixture resulted in acetylation that was similar to the rate of PCAF alone (compare bar 1 and bar 4) whereas in the presence of H3-CoA-20, the PCAF/p300 mixture resulted in acetylation that was similar to the rate of p300 alone (compare bar 2 and bar 5). Moreover, addition of both Lys-CoA and H3-CoA-20 to the PCAF/p300 mixture abolished nearly completely histone acetylation (bar 6). Furthermore, the pattern of histone acetylation (histone H3 vs. H4) reflected that expected for PCAF in the presence of Lys-CoA and that expected for p300 in the presence of H3-CoA-20 (data not shown). These results suggest that with purified histone mixtures, PCAF and p300 act independently when present together (without synergism or antagonism) to acetylate histones.

Given that physiologic substrates for p300 and PCAF are likely to be histones bound to DNA in nucleosomal structure, it was important to establish that selectivity of the inhibitors Lys-CoA and H3-CoA-20 could be achieved in this setting. As nucleosomes are much poorer substrates for HAT enzymes compared to free histones, it was necessary to use larger quantities of each of the enzymes (~5–10-fold greater) and allow acetylation to take place for a longer period of time (~40-fold greater) to achieve adequate signal to noise. In this way it was shown that Lys-CoA was still selective for p300 inhibition and H3-CoA-20 was still selective for PCAF blockade (using 20 µM Lys-CoA, greater than 90% p300 inhibition was achieved while less than 10% PCAF inhibition occurred; using 15 µM H3-CoA-20, greater than 90% PCAF inhibition was observed with less than 10% p300 inhibition detected, data not shown). Experiments with mixtures of PCAF and p300 and nucleosome substrate showed the same pattern of histone acetylation in the presence of inhibitors as observed for the free histone substrates (compare FIG. 3A and 3B). Thus it can be concluded the p300 and PCAF act independently in histone acetylation of nucleosomes as substrates. This is noteworthy since higher concentrations of HATs were used in the nucleosome experiments, which would be expected to encourage p300-PCAF interaction.

An important application of selective HAT inhibitors is to use them as tools in studies of transcriptional regulation. Given the limited ability of CoA conjugates to penetrate cell membranes (Robishaw and Neely, 1985), it was advantageous to evaluate these compounds in an in vitro chromatin-based transcription system. In this regard, we exploited a recently developed in vitro chromatin-transcription system that appears to require the HAT activity of full length p300 for the function of transcriptional activators (data not shown). The strategy designed for these experiments is outlined in FIG. 4A.

The chromatin template was reconstituted by incubation of purified proteins (HeLa core histones, NAP1 and rh TopoI) with a 5.4 kb plasmid (p20855G5MLC2AT) that contains a 690 bp promoter region (5 Gal4 binding sites and the adenovirus major late promoter with a G-less cassette) flanked on both sides by the 5 nucleosome positioning sequence from the sea urchin 55 rRNA gene (Cote et al., 1995). Assembled chromatin was structurally characterized by supercoiling and micrococcal nuclease (MNase) assay (data not shown).

Figure 4A:
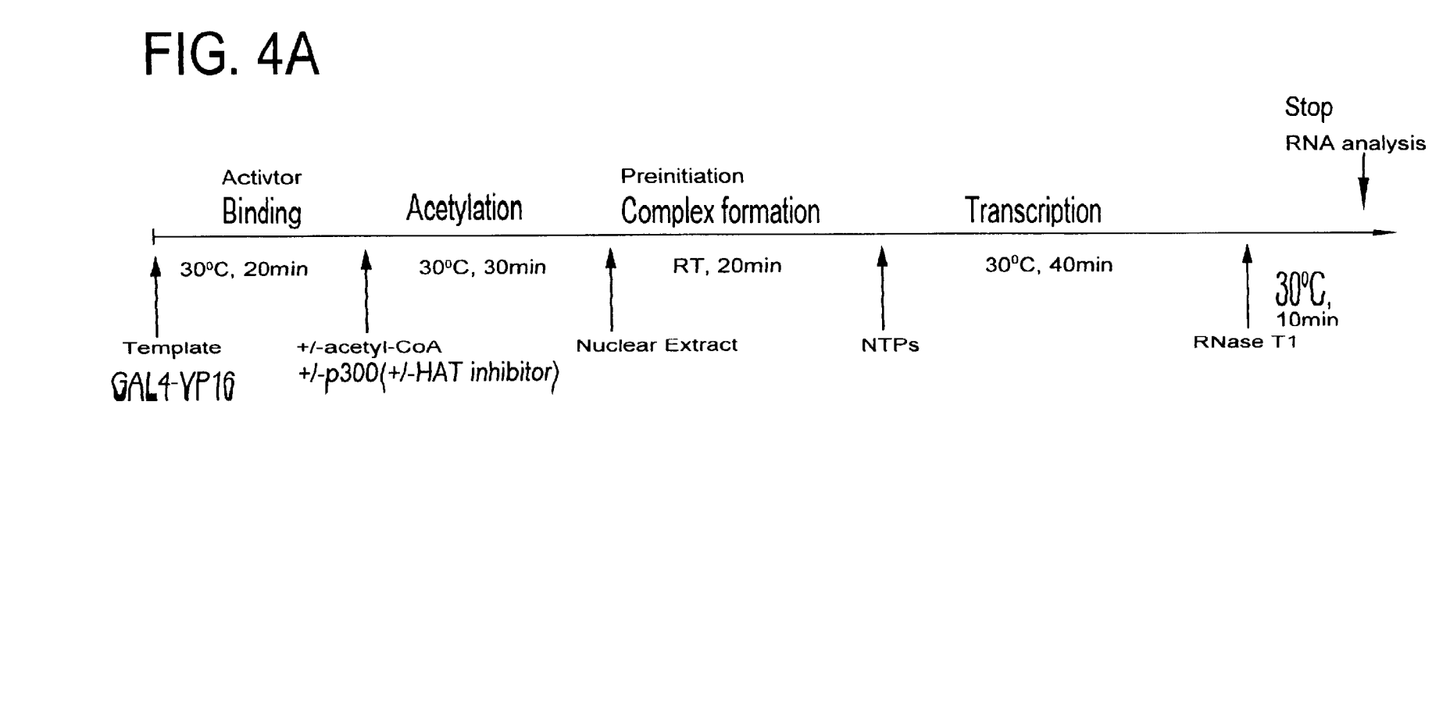
FIG. 4A: Outline of the in vitro transcription protocol.
Figure 4B:
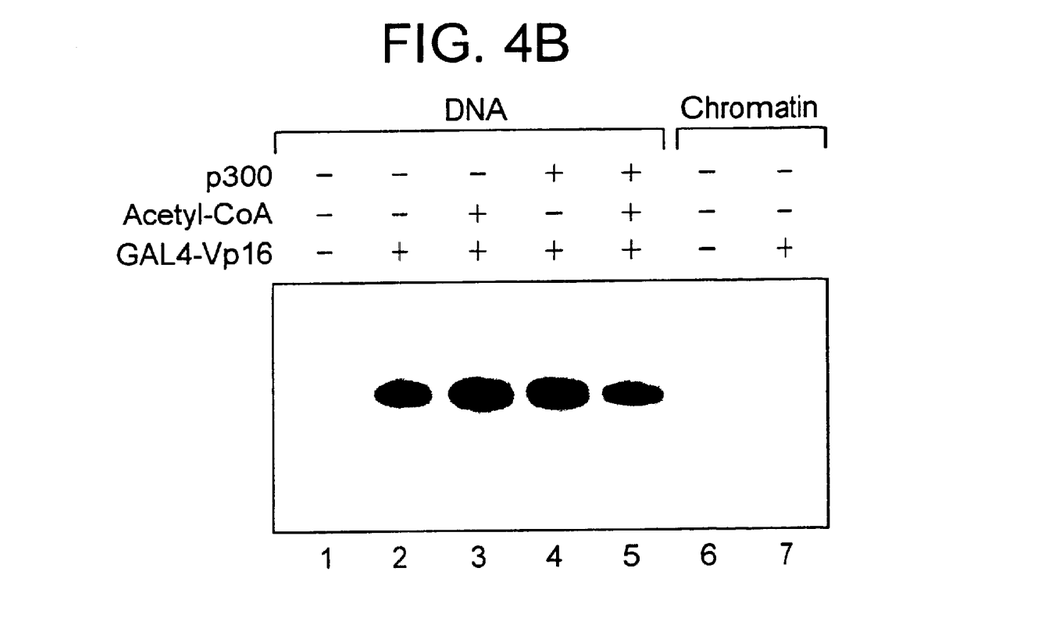
FIG. 4B and C: Transcription from naked DNA and chromatin templates. DNA (28 ng) and freshly assembled chromatin templates (with an equivalent amount of DNA) were incubated with or without activator, Gal4-VP16 (30 ng) for 20 min at 30° C.; 25 ng of baculovirus expressed, highly purified p300 (full length) and 1.5 $\mu$M of acetyl-CoA were added as indicated. Following the addition of nuclear extract (source of general transcription factors) and NTPs, transcription reactions were incubated and processed as described. Before adding it to the reaction, p300 was incubated (4° C., 20 min) with or without inhibitors: without inhibitor (panel C, lanes 2 and 9), 10 $\mu$M Lys-CoA (panel C, lanes 3 and lane 10) or H3-CoA-20 (Panel C, lanes 4 and 11).
Figure 4C:
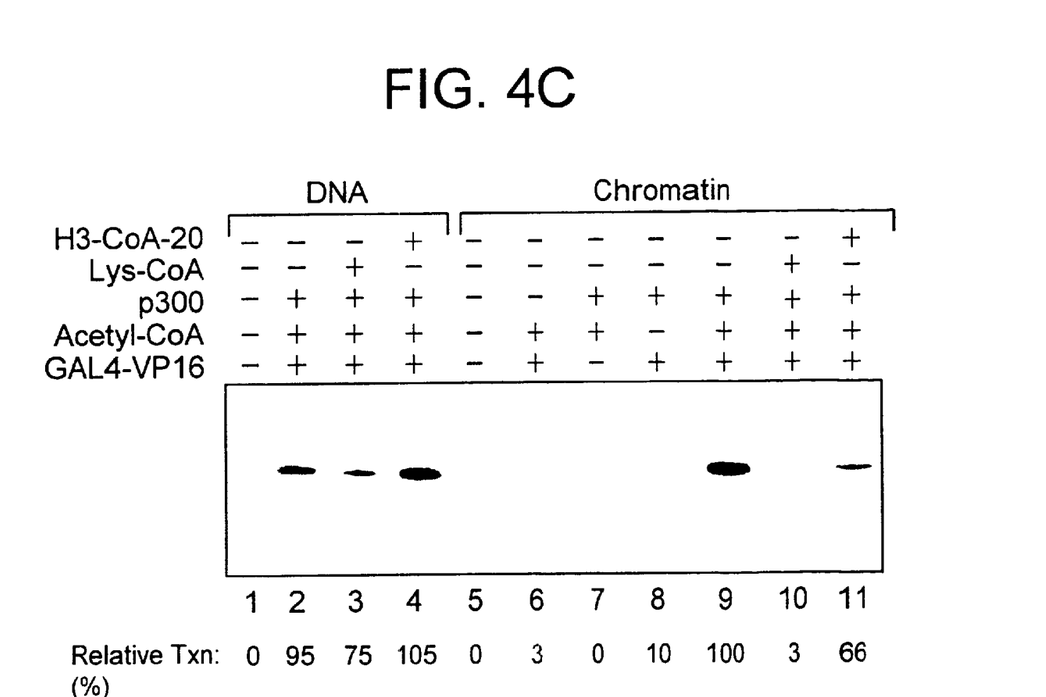
Figure 5:
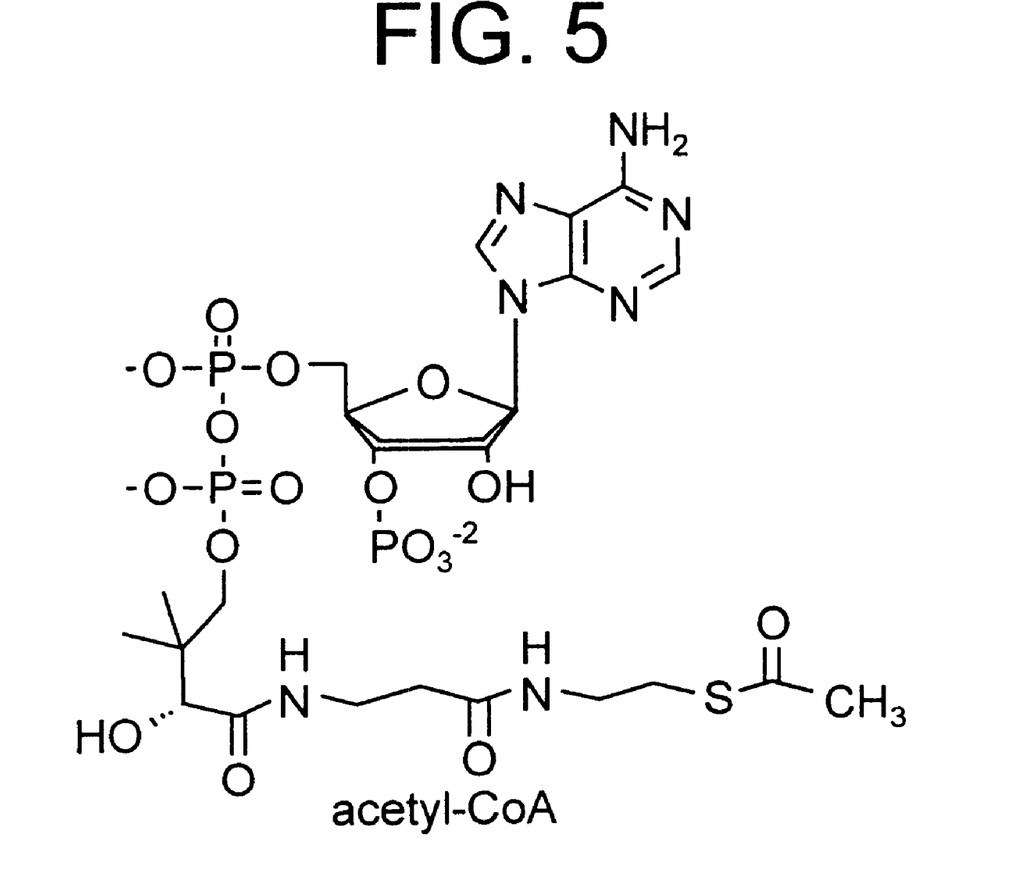
FIG. 5. Acetyl-CoA.

The chromatin template was nearly completely inert even in the presence of Gal-VP16 activator (FIG. 4B, lane 7). In contrast, an equimolar amount of the corresponding DNA template showed a high level of activator-dependent transcription that was 15-fold above the basal transcription (FIG. 4B, lanes 1 vs 2) and independent of the presence of p300 and/or acetyl-CoA (FIG. 4B, lane 2 vs 3–5). Addition of p300 along with Gal-VP16 activator had a negligible effect in activating transcription from the chromatin template (FIG. 4C, lane 8). However, addition of 1.5 µM acetyl-CoA along with p300 and Gal-VP16 activator increased transcription ~10-fold compared to the reaction without acetyl-CoA addition (compare FIG. 4C, lanes 8 vs 9), suggesting a role for the p300 HAT activity in the observed transcription activation.

Preincubation of p300 with the p300 selective HAT inhibitor Lys-CoA (10 µM) completely abolished the p300 and acetyl-CoA dependent transcription activation from the chromatin template (FIG. 4C, lanes 10 vs 9). Similar pretreatment of p30 with the PCAF selective inhibitor, H3-20-CoA (10 μM) marginally inhibited (~30%) the p300 HAT activity dependent transcription (FIG. 4C, lanes 9 vs 11) consistent with the expected specificity of the inhibitors. As a control, it was shown that the effect of these two inhibitors on naked DNA transcription was minimal, Lys-CoA inhibited naked DNA transcription only 15–20% (average of 4 independent experiments) and H3-20-CoA did not affect transcription at all (FIG. 4C, lanes 2 vs 3 and 4). These data establish directly the role of p300 HAT activity in this transcriptional system.

Further studies showed that baculovirus expressed full length PCAF had no effect on activator dependent transcription from the chromatin template in either the presence or absence of p300 under the conditions we have tested (data not shown). It was a formal possibility that PCAF could be recruited to the promoter in the presence of p300, and provide a redundant HAT function that did not further increase transcription. However, this possibility was ruled out by showing that Lys-CoA abolished transcriptional activation in the presence of p300-PCAF mixtures just as it did with p300 alone (data not shown).

In summary, these studies report the design, synthesis, and evaluation of the first selective HAT inhibitors. These HAT inhibitors were used to quantify the contributions of the interacting HATs p300 and PCAF in histone acetylation and revealed an additive but non-synergistic interaction between the PCAF and p300 HAT activities in the systems investigated. Furthermore, the p300-selective inhibitor, Lys-CoA, showed a specific inhibition of p300 and acetyl-CoA dependent transcription from a chromatin template, directly demonstrating the importance of the p300 HAT activity in transcriptional enhancement in an in vitro system. Applications employing selective HAT inhibitors as biological tools in a variety of contexts can now be pursued.

Experimental procedures

Lys-CoA synthesis

Synthesis of Lys-CoA was carried out as follows: N-acetyl-lysine-amide hydrochloride (Ac-Lys-NH$_2$, 50 mg, 224 mmol), bromoacetic acid (31 mg, 224 mmol), 1-[3-(dimethylamino)propyl]-3-ethylcarbodiimide hydrochloride (EDC, 43 mg, 224 mmol), and triethylamine (31.1 ml, 224 mmol) were dissolved in 4 mL N,N-dimethylformamide (DMF). After stirring under nitrogen at room temperature (12 h), more bromoacetic acid (31 mg, 224 mmol) and EDC (43 mg, 224 mmol) were added to the reaction. After an additional 4 h, the mixture was concentrated in vacuo. The residue was dissolved in 4 mL aqueous 1 M triethylammonium bicarbonate (pH 8.0)/4 mL methanol, CoASH (129 mg, 155 mmol) was added, and the reaction was stirred overnight under nitrogen for a total of 15 hours, Lys-CoA was purified from this solution by preparative reverse phase C-18 HPLC. The compound was eluted ($t_R$=30 min, λ=260 nm) at a constant flow rate of 10 mL/min with 100% aqueous 50 mM KH$_2$PO$_4$ (pH 4.5) for 5 minutes, followed by a linear gradient to 40% methanol over 35 minutes, Lys-CoA was desalted by preparative C-18 HPLC at a constant flow rate of 10 mL/min, eluting with 100% H$_2$O (0.05% TFA) for 30 min, followed by a linear gradient to 100% methanol over 5 min. then 100% methanol for 20 min to elute the compound ($t_R$=41 min). The methanol was removed on a rotary evaporator and the compound was dissolved in H$_2$O and lyophilized for 48 hr. The compound (51 mg, 23% yield) appeared >95% pure by analytical reversed phase C-18 HPLC. $^1$H NMR (400 MHz, D$_2$O), and electrospray mass spectrometry, which showed data in full accord with the reported structure.

Peptide CoA Conjugate Syntheses

Peptide CoA conjugates and other peptides (H3-CoA-7, H4-CoA-7, H3-CoA-20, H4-CoA-20, H3-20, H4-20) were synthesized using the solid phase fluorenylmethoxycarbonyl peptide synthesis strategy on a Rainin PS-3 machine. The N-terminal residues were used in the α-amino acetylated forms and the C-terminal residues were the free acids for the 20 aa peptides (obtained with Wang resin) and the carboxamides for the 7 aa peptides (obtained with Rink amide resin). Note that lysine residues that were not conjugated with CoA were orthogonally protected with Dde (dimethyldioxocyclohexylidene) ε-NH$_2$ group) whereas the others were protected with tert-butoxycarbonyl groups. Peptides were cleaved from the resin and deblocked with trifluoroacetic acid in reagent K which left the Dde group intact and then reacted as described above with excess bromoacetic acid (~4 equivalents) and CoASH (~5 equivalents), followed by Dde removal via hydrazinolysis (3% aqueous hydrazine at room temperature, 2–3 h). For standard peptides (H3-20 and H4-20), Dde groups were removed without carrying out the CoA coupling steps. Peptides were purified by preparative reversed phase C-18 HPLC (H$_2$O:CH$_3$CN: 0.5% trifluoroacetic acid). Peptides appeared >95% pure using analytical reversed phase C-18 HPLC and showed the predicted molecular mass using electrospray mass spectrometry.

HAT Activity Inhibition Assays

Full length PCAF and p300 proteins were prepared and purified according to previously described methods (Schiltz et al., 1999). HAT inhibition assay procedures were adapted from previously described methods (gryzko et al., 1996; Yang et al., 1996; Schiltz et al., 1999). Briefly, substrate concentrations were 10 μM acetyl-CoA (NEN, $^{14}$C, 0.02 μCi/μL), 33 μg/mL mixed histones (Boehringer); buffer conditions-50 mM Tris-HCl (pH 8), 10 mM sodium butyrate 1 mM phenylmethyl sulfonyl fluoride, 1 mM dithiothreitol, 0.1 mM N,N,N',N'-ethylenediamine tetraacetic acid and 10% v/v glycerol. Reactions employed purified recombinant p300 and PCAF (Schiltz et al., 1999) at concentrations of 6 nM and 27 nM, respectively. A range of at least 5 inhibitor concentrations were used. Assays were carried out in 0.5 mL plastic tubes at 30° C. and the reaction volumes were 30 μL. Reactions were initiated with the radioactive acetyl-CoA (4 μL) after allowing the enzyme/buffer/histone/inhibitor mixture to equilibrate at 30° C. for 10 min, and reactions quenched after 1 min with 7.5 μL 5×SDS gel load. Mixtures were run out on 15% SDSPAGE visualized with Coomassie blue, dried, and radioactivity quantified by phosphorimage analysis (Molecular Dynamics). In all cases, background acetylation (in the absence of enzyme) was subtracted from the total signal. All assays were performed at least twice and duplicates generally agreed within 20%. IC$_{50}$ values were estimated from bar graph plots (see FIG. 2 for an example) and estimated standard errors on these values are ±20%. For nucleosomes (Cote et al., 1995), enzyme concentrations were 24 nM for p300 and 432 nM for PCAF and reactions were allowed to proceed for 40 min before quenching (nucleosome concentrations had approximately equal amount of protein visualized by SDSPAGE as the mixed histone reactions).

Transcription studies

Native HeLa nucleosome was prepared as described elsewhere (Cote et al., 1995). Human core histones were purified as described elsewhere (Kunda et a, 1998). Recombinant His$_6$-tagged nucleosome assembly protein 1 (NAP1) and transcription activator Gal4-VP16 were expressed in *E. coli* and purified with nitrilloacetic acid-agarose (Qiagen) as specified by the manufacturer. Baculovirus expressed recombinant human topoisomerase I (rh TopoI) and full length p300 were purified as described previously (Wang and Roeder, 1996; Kraus and Kadonaga, 1998). Chromatin template for transcription studies were assembled on a ~5.4 kb plasmid (p2085S G5MLC2AT) with purified human core histones, rh TpopI, and NAP1 as described (T. K. K. et al., manuscript in preparation). Prior to use in the transcription experiment, assembled, chromatin was subjected to supercoiling and Mnase assay. In vitro transcription assays were carried out in 50 $\mu$L reaction mixtures containing either 28 ng of DNA or an equivalent amount of chromatin.

Summary

Here we described the design, synthesis, and application of peptide CoA conjugates as selective HAT inhibitors for the transcription factors p300 and PCAF. Two inhibitors (Lys-CoA for p300, H3-CoA-20 for PCAF) were found to be potent ($IC_{50}$~0.5 $\mu$M) and selective (~200-fold) in blocking p300 and PCAF HAT activity. These inhibitors were used to show quantitatively that PCAF and p300 display additive but not synergistic HAT activity when present in mixtures. Lys-CoA was used to directly demonstrate the importance of p300 HAT activity in enhancing chromatin template mediated transcription in vitro.

References

Bannister, A. J., and Kouzarides, T. (1996) The CBP co-activator is a histone acetyltransferase, Nature 384, 641–643.

Coon, S. L., Roseboom, P. H., Baler, R., Weller, J. L., Namboodiri, M. A. A., Koonin, E. V. and Klein, D. C. (1995) Pineal serotinin N-acetyltransferase: expression cloning and molecular analysis. Science 270, 1681–1683.

Cote, J., Utley, R. T., and Workman, J. L. (1995) Basic analysis of transcription factor binding to nucleosomes. Meth. Mol. Genet. 6, 108–152.

Cullis, P. M., Wolfenden, R., Cousens, L., and Alberts, B. M. (1982) Inhibition of histone acetylation by N-[2-(S-Coenzyme A)acetyl] spermidine amide, a multisubstrate analog. J. Biol. Chem. 257, 12165–12169.

DeAngelis, J., Gastel, J., Klein, D. C. and Cole, P. A. (1998) Kinetic analysis of the catalytic mechanism of serotonin N-acetyltransferase. J. Biol. Chem. 273, 3045–3050.

Dutnall, R. N., Tafrov S. T., Sternglanz, R., and Ramakrishnan, V. (1998) Structure of the histone acetyltransferase Hat1: a paradigm for the GCN5-related N-acetyltransferase superfamily. Cell 94, 427–438.

Erwin, B. G., Persson, L., and Pegg, A. E. (1984) Differential inhibition of histone and polyamine acetylases by multisubstrate analogs. Biochemistry 23, 4250–4255.

Giles, R. H., Peters, D. J. M., and Breuning, M. H. (1998) Conjunction dysfunction: CBP/p300 in human disease. Trends in Genetics 14, 178–182.

Gu, W., and Roeder, R. G. (1997) Activation of p53 sequence-specific DNA binding by acetylation of the p53 C-terminal domain. Cell 90, 593–606.

Hickman, A. B., Klein, D. C., and Dyda, F. (1999a) Melatonin biosynthesis: the structure of serotonin N-acetyltransferase at 2.5 Å resolution suggests a catalytic mechanism. Mol. Cell 3, 23–32.

Hickman, A. B., Namboodiri, M. A., Klein, D. C., and Dyda, F. (1999b) The structural basis of ordered substrate binding by serotonin N-acetyltransferase: enzyme complex at 1.8 Å resolution with a bisubstrate analog. Cell 97, 361–369.

Khalil, E., and Cole, P. A. (1998) A potent inhibitor of the melatonin rhythm enzyme. J. Am. Chem. Soc. 120, 6195–6196.

Khalil, E., De Angelis, J., Ishii, M., and Cole. P. A. (1999) Mechanism-based inhibition of the melatonin rhythm enzyme: pharmacologic exploitation of active site functional plasticity. Proc. Natl. Acad. Sci. U.S.A. October 26 issue.

Korzus, E., Torchia, J., Rose. D. W., Xu, L., Kurokawa, R., McInerney, E. M., Mullen, T. M., Glass, C. K., and Rosenfeld M. G. (1998) Transcription factor-specific requirements for coactivators and their acetyltransferase functions. Science 279, 703–7.

Kraus, L. W., and Kadonaga J. T. 1998, p300 and estrogen receptor cooperatively activate transcription via differential enhancement of initiation and reinitiation. Genes & Dev. 12, 331–342.

Kundu, T. K., Wang, Z., and Roeder, R. G. (1999) Human TFIIIC relieves chromatin-mediated repression of RNA polymerase III transcription and contains an intrinsic histone acetyltransferase activity. Mol. Cell. Biol. 19, 1605–1615.

Lin. Y., Fletcher, C. M., Zhou, J., Allis, C. D., and Wagner, G. (1999) Solution structure of the catalytic domain of GCN5 histone acetyltransferase bound to coenzyme A. Nature 400, 86–89.

Mizzen, C. A. and Allis, C. D. (1998) Linking histone acetylation to transcriptional regulation. Cell. Mol. Life Sci. 54, 6–20.

Neuwald, A. F., Landsman, D. (1997) GCN-5-related histone N-acetyltransferase belong to a diverse superfamily that includes the yeast SPT10 protein. TIBS, 22, 154–155.

Ogryzko, V. V., Schiltz, R. L., Russanova, V., Howard, B. H., Nakatani, Y. (1996) The transcriptional coactivators p300 and CBP are histone acetyltransferases. Cell 87, 953–959.

Puri, P. L., Sartorelli, V., Yang, X.-J., Hamamori, Y., Ogryzko, V. V., Howard, B. H., Kedes, L., Wang, J. Y. J., Graessmann, A., Nakatani, Y. and Levrero, M. (1997) Differential roles of p300 and PCAF acetyltranferases in muscle differentiation. Mol. Cell 1, 35–45.

Robishaw, J. D., and Neely, J. R. (1985) Coenzyme A metabolism. Am. J. Physiol. 248, E1–E9.

Rojas, J. R., Trievel, R. C., Zhou, J., Mo, Y., Li, X., Berger. S. L., Allis, C. D., and Marmorstein, R. (1999) Structure of Tetrahymena GCN5 bound to coenzyme A and a histone H3 peptide. Nature 401, 93–98.

Schiltz, R. L., Mizzen, C. A., Vassilev, A., Cook, R. G., Allis, C. D., and Nakatani, Y. (1999) Overlapping but distinct patterns of histone acetylation by the human coactivators p300 and PCAF within nucleosomal substrates. J. Biol. Chem. 274, 1189–1192.

Struhl, K. (1998) Histone acetylation and transcriptional regulatory mechanisms. Genes & Dev. 12, 599–606.

Tanner, K. G., Trievel, R. C., Kuo, M.-H., Howard, R. M., Berger, S. L., Allis, C. D., Marmorstein, R., and Denu, J. M. (1999) Catalytic mechanism and function of invariant glutamic acid 173 from the histone acetyltransferase GCN5 transcriptional coactivator. J. Biol. Chem. 274, 18157–18160.

Taunton, J., Hassig, C. A., and Schreiber, S. L. (1996) A mammalian histone deacetylase related to the yeast transcriptional regulator. Science 272, 408–411.

Wang, Z., and R. G. Roeder 1996. TFIIIC1 acts through a downstream region to stabilize TFIIIC2 binding to RNA polymerase III promoters. Mol. Cell. Biol. 16, 6841–6850.

Wolf, E., Vassilev, A., Makino, Y., Sali, A., Nakatani, Y., and Burley, S. K. (1998) Crystal structure of a GCN5-related N-acetyltransferase: Serratia marcescens aminoglycoside 3-N-acetyltransferase. Cell 94, 439–449.

Wybenga-Groot, L. E., Draker, K.-a., Wright, G. D., and Berghuis, A. M. (1999) Crystal structure of an aminoglycoside 6'-N-acetyltransferase defining the GCN5-related N-acetyltransferase superfamily fold. Structure 7, 497–507.

Yang, X.-J., Ogryzko, V. V., Nishikawa, J., Howard, B. H., and Nakatani, Y. (1996) A p300/CBP-associated factor that competes with the adenoviral oncoprotein E1A. Nature 382, 319–324.

Figure Legends

1) FIG. 1. Design and Synthesis of Peptide CoA Conjugates. (A) General scheme for CoA coupling to the lysine $\epsilon$-NH2 groups. (B) Peptide CoA conjugates evaluated for HAT inhibition. See Experimental Procedures for synthetic details.

Figure 2A:
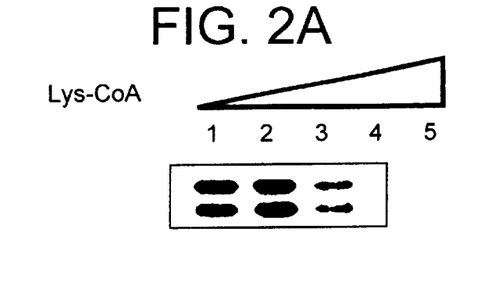
FIG. 2A: Autoradiographic analysis of p300 HAT inhibition by Lys-CoA. Lanes 1–5 employed 0, 0.1, 0.5, 2.5, and 10 μM concentrations of Lys-CoA. Images bands are histones H4 (top) and H3 (bottom).
Figure 2B:
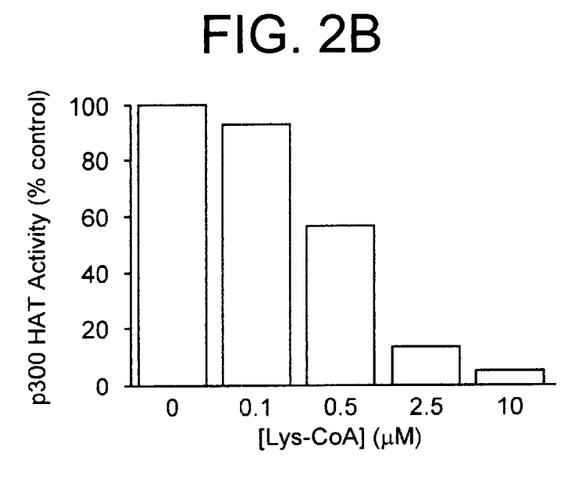
FIG. 2B: Bar graph analysis of p300 HAT Inhibition by Lys-CoA at the concentrations indicated, quantitated using Phosphorimage analysis (Molecular Dynamics). HAT activity is normalized to 100% for no added inhibitor.
Figure 2C:
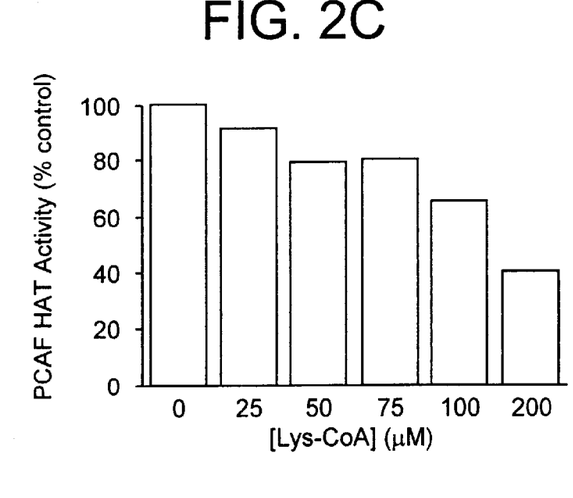
FIG. 2C: Bar graph analysis of PCAF HAT Inhibition by Lys-CoA at the concentrations indicated, quantitated using Phosphorimage analysis (Molecular Dynamics). HAT activity is normalized to 100% for no added inhibitor. Standard error was found to be ±20% for duplicate runs.

2) FIG. 2. Evaluation of Lys-CoA as a HAT Inhibitor. (A) Autoradiographic analysis of p300 HAT inhibition by Lys-CoA. Lanes 1–5 employed 0, 0.1, 0.5, 2.5, and 10 $\mu$M concentrations of Lys-CoA. Imaged bands are histones H4 (top) and H3 (bottom). See Experimental Procedures for details. (B) Bar graph analysis of p300 HAT Inhibition by Lys-CoA at the concentrations indicated, quantitated using Phosphorimage analysis (Molecular Dynamics). HAT activity is normalized to 100% for no added inhibitor. (C) Bar graph analysis of PCAF HAT Inhibition by Lys-CoA at the concentration indicated, quantitated using Phosphorimage analysis (Molecular Dynamics). HAT activity is normalized to 100% for no added inhibitor. Standard error was found to be ±20% for duplicate runs.

Figure 3B:
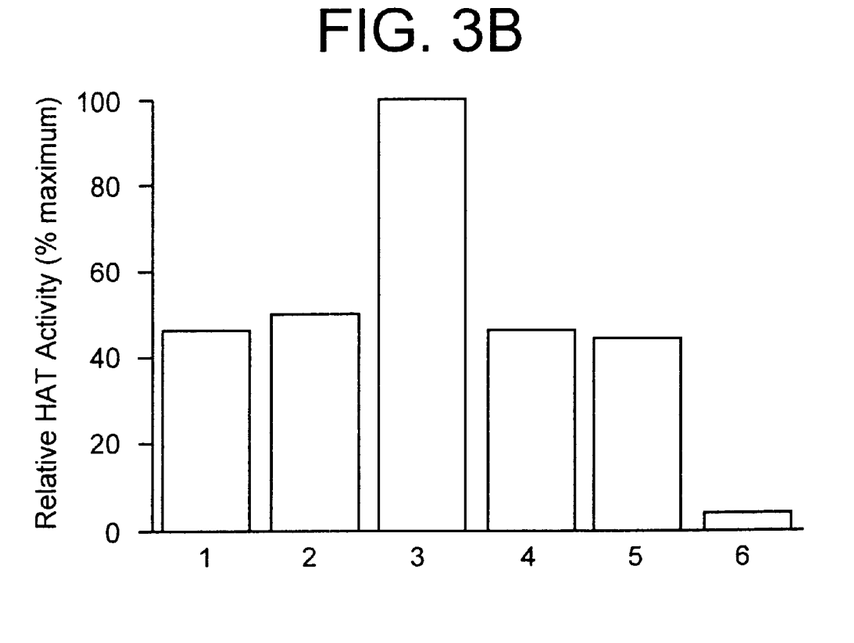
FIG. 3B: p300 and PCAF HAT activities with nucleosomes as substrates. Bar 1, PCAF alone without inhibitors; Bar 2, p300 alone without inhibitors; Bar 3; PCAF+p300 without inhibitors; Bar 4, PCAF+p300+Lys-CoA (20 $\mu$M); Bar 5, PCAF+p300+H3-CoA-20 (15 $\mu$M); Bar 6, PCAF+p300+Lys-CoA (20 $\mu$M)+H3-CoA-20 (15 $\mu$M). Activities were normalized to 100% for Bar 3. Standard error was found to be ±20% for duplicate runs.

3) FIG. 3. Assessment of p300 and PCAF HAT Activities in p300/PCAF Mixtures. (A) p300 and PCAF HAT activities with mixed histones as substrates. Bar 1, PCAF alone without inhibitors; Bar 2, p300 alone without inhibitors; Bar 3; PCAF+p300 without inhibitors; Bar 4, PCAF+p300+Lys-CoA (30 $\mu$M); Bar 5, PCAF+p300+H3-CoA-20 (20 $\mu$M); Bar 6, PCAF+p300+Lys-CoA (30 $\mu$M)+H3-CoA-20 (30 $\mu$M). Activities were normalized to 100% for Bar 3. Standard error was found to be ±20% for duplicate runs. In a separate experiment done under identical conditions with the individual enzymes, it was shown that Lys-CoA (20 $\mu$M) and H3-CoA-20 (15 $\mu$M) blocked p300 and PCAF HAT activity greater than 90%, respectively, and showed less than 10% inhibition with PCAF and p300, respectively (data not shown). See Experimental Procedures for details. (B) p300 and PCAF HAT activities with nucleosomes as substrates. Bar 1, PCAF alone without inhibitors; Bar 2, p300 alone without inhibitors; Bar 3; PCAF+p300 without inhibitors; Bar 4, PCAF+p300+Lys-CoA (20 $\mu$M); Bar 5, PCAF+300+H3-CoA-20 (15 $\mu$M); Bar 6, PCAF+p300+Lys-CoA (20 $\mu$M)+H3-CoA-20 (15 $\mu$M). Activities were normalized to 100% for Bar 3. Standard error was found to be ±20% for duplicate runs. In a separate experiment done under identical conditions with the individual enzymes, it was shown that Lys-CoA (20 $\mu$M) and H3-CoA-20 (15 $\mu$M) blocked p300 and PCAF nucleosome acetylation activity greater than 90%, respectively, and showed less than 10% inhibition with PCAF and p300, respectively (data now shown) See Experimental Procedures for details.

4) FIG. 4. Lys-CoA inhibits p300 HAT activity dependent transcription activation. (A) Outline of the in vitro transcription protocol. (B) and (C) Transcription form naked DNA and chromatin templates. DNA (28 ng) and freshly assembled chromatin templates (with an equivalent amount of DNA) were incubated with or without activator, Gal4-VP16 (30 ng) for 20 min at 30°, 25 ng of baculovirus expressed, highly purified p300 (full length) and 1.5 $\mu$M of acetyl-CoA were added as indicated. Following the addition of nuclear extract (source of general transcription factors) and NTPs, transcription reactions were incubated and processed as described (T. K. K. et al., manuscript in preparation). Before adding it to the reaction, p300 was incubated (4° C., 20 min) with or without inhibitors; without inhibitor (pane C, lanes 2 and 9), 10 $\mu$M Lys-CoA (panel C, lanes 3 and lane 10) or H3-CoA-20 (Panel C, lanes 4 and 11).

TABLE 1

| Compound | IC$_{50}$ with p300 ($\mu$M) | IC$_{50}$ with PCAF ($\mu$M) |
| --- | --- | --- |
| CoASH | 200 | >20 |
| H3-20 | — | >20 |
| H3-CoA-7 | >30 | >20 |
| H3-CoA-20 | 200 | 0.3 |
| H4-CoA-20 | >10 | >10 |
| Lys-CoA | 0.5 | 200 |

Table 1 provides IC$_{50}$ values for synthetic compounds with CoASH. Substrate concentrations were: [acetyl-CoA]= 10 M, [mixed histones]=33 $\mu$g/mL. Assays were performed as described in Experimental Procedures. The IC$_{50}$ values are identified as the concentrations of compound necessary to cause 50% inhibition of the acetyltransferase reaction. The values written as '>10 $\mu$M' or '>20 $\mu$M' indicate that less than 50% inhibition was observed at these inhibitor concentrations (the upper limit used in the particular assay). Standard errors on all values are estimated to be ±20%.

What is claimed is:

1. A compound of the formula wherein $R_8$ is methyl, $R_9$ is hydrogen, n is 2, $R_1$ is H, $R_2$ is H, $R_{10}$ is H, and each of the two $R_{11}$ groups are H, said compound also referred to as Lys-CoA.

2. A compound of the formula wherein $R_8$ is (N-acetyl)-Ala-Thr-Lys-Gln-Thr-Ala-Arg-Lys-Ser-Thr-Gly-NH-CH2—, $R_9$ is the polypeptide Ala-Pro-Arg-Lys-Gln-Leu in that sequence, n is 2, $R_1$ is H, $R_2$ is H, $R_{10}$ is H, and each of the two $R_{11}$ groups are H, said compound also referred to as H3-CoA-20, the peptide portion of $R_8$ being referred to as SEQ ID NO:7 and $R_9$ being referred to as SEQ ID NO:4.

* * * * *